(12) United States Patent
Sykes

(10) Patent No.: US 6,341,530 B1
(45) Date of Patent: Jan. 29, 2002

(54) APPARATUS AND METHOD FOR SHEAR TESTING BONDS OF ELECTRICAL CONNECTIONS

(75) Inventor: Robert Sykes, Tenoring (GB)

(73) Assignee: Dåge Precision Industries, Ltd., Buckinghamshire (GB)

(*) Notice: Subject to any disclaimer, the term of this patent is extended or adjusted under 35 U.S.C. 154(b) by 0 days.

(21) Appl. No.: 09/564,171

(22) Filed: May 3, 2000

(30) Foreign Application Priority Data

May 6, 1999 (GB) ................................ 9910362

(51) Int. Cl.[7] ................................................ G01N 3/08
(52) U.S. Cl. ........................................ 73/831; 73/842
(58) Field of Search ........................ 73/827, 826, 830, 73/831, 833, 835, 841, 842, 845

(56) References Cited

U.S. PATENT DOCUMENTS 5,337,614 A  * 8/1994  Jiang et al. ................... 73/827
5,641,913 A  * 6/1997  Watanabe ...................... 73/827
5,892,155 A  * 4/1999  Vanderlip ...................... 73/827
5,894,981 A  * 4/1999  Kelly ............................ 228/104
5,969,262 A  * 10/1999 Ino et al. ....................... 73/827
6,117,695 A  * 9/2000  Murphy et al. ................ 438/15

* cited by examiner

*Primary Examiner*—Max Noori
(74) *Attorney, Agent, or Firm*—Kilpatrick Stockton LLP

(57) ABSTRACT

A device is described for testing the force to shear a deposit of solder or gold from a substrate, these deposits having a diameter in the range 50–100 $\mu$m and being for the bonding of electrical conductors. A shear tool has a semi-cylindrical cavity which closely approximates to the mean diameter of a range of substrates. This tool is adapted to re-shape substrates for a better fit, re-shaping occurring over 30% or less of the circumference of a deposit, and to a depth of 10% or less of the diameter of the substrate.

10 Claims, 2 Drawing Sheets

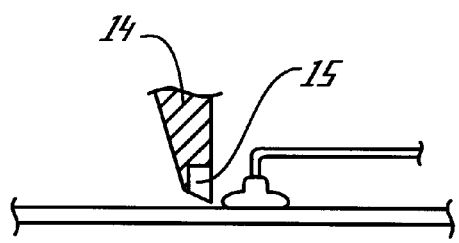 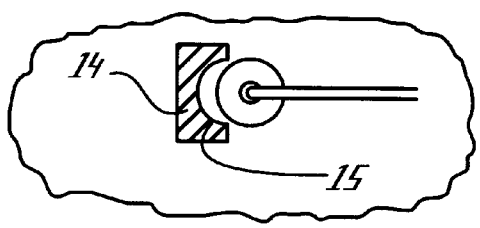
Fig. 6    Fig. 7
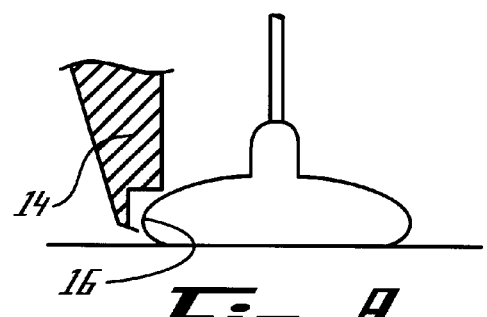 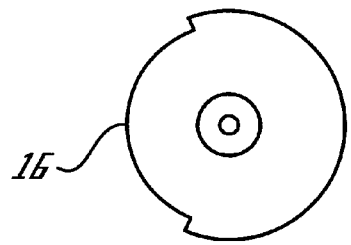
Fig. 8    Fig. 9
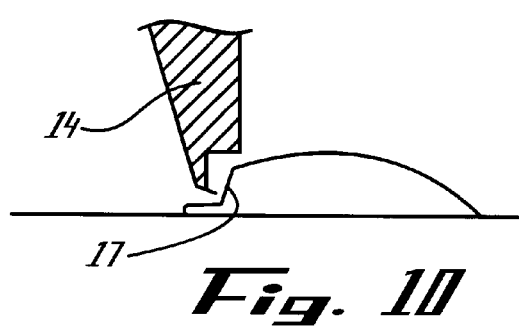 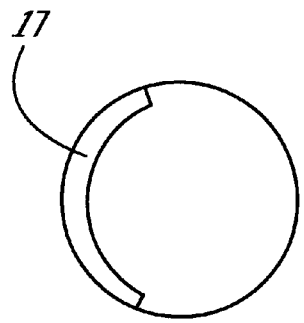
Fig. 10    Fig. 11

APPARATUS AND METHOD FOR SHEAR TESTING BONDS OF ELECTRICAL CONNECTIONS

This invention concerns a device for testing the integrity of a bond in a semi-conductor device, and more particularly the strength of a bond between a substrate and a means of electrical connection thereto, typically a part-spherical deposit of solder or gold.

Semiconductor devices are very small, typically from 0.2 mm square to 15 mm square. These devices have sites for the bonding of electrical conductors thereto Sites typically comprise part spherical deposits of gold or solder, collectively known as balls, which in use have the appearance of a low circular dome, and a diameter in the range 50–1000 $\mu$m. These deposits form part of the electrical path between, for example, a printed circuit board and a chip, and may directly connect components, or may be joined to a wire which is itself connected to another component.

In the case of gold, the ball may comprise the balled end of a gold wire which is joined to an electrical path by a thermocompression technique. In the case of solder, a discrete ball may be applied to a substrate and reflowed to form a semi-circular bump for subsequent connection to another component.

It is necessary to test the mechanical strength of the interermetallic bond between the gold or solder deposit and the substrate in order to give confidence that the bonding method is adequate, and that the bond strength is sufficient. Difficulties arise because of the very small dimensions of the components, the precision with which the testing device must be positioned, and the very small forces and deflections which are to be measured.

It has been proposed to test such deposits by applying a flat shear tool to one side thereof. In order to avoid friction caused by the tool rubbing on the surface of the substrate, it is necessary for the tool to be just above the substrate surface. The height of the tool must be closely controlled to give accurate force measurement, typically within ±0.001 mm. The flat shear tool typically makes an initial point contact with the deposit, and that contact may be poor due to the curvature of the deposit. The initial contact may result in deformation of the deposit due to the high point load, and this may cause a mechanical failure of the deposit before a significant load is applied to the bond. Breakage of the deposit may be due to cutting in by the shear tool. If this happens information concerning the ultimate bond strength cannot be obtained.

The gold ball provides a particular problem because alternative techniques, such as a tensile test using mechanical tweezers, are not possible due to the very small diameter of a typical gold deposit.

What is required is a better means for shear testing which can overcome the aforementioned problems, particularly those problems associated with the very small diameter of a typical gold deposit. The principal objective is to maximise the load which can be applied to the intermetallic interface.

According to the invention, there is provided a test device for shear testing of electrical conduction deposits of semiconductor devices, said deposits being dome-like and having a diameter in the range 50–1000 $\mu$m, said test device comprising a test head having a recess adapted to closely engage said deposit over part of the circumference thereof for the application of a shear force.

Typical deposits are soft electrical conduction materials such as solder and gold.

The recess may closely engage the deposit over part of the surface thereof, for example a part-spherical surface.

Preferably the recess is semicircular and cylindrical. Such a recess is relatively easy to manufacture compared with, for example, a part spherical recess. In any event the test head should engage the deposit over sufficient area to ensure that shearing at the bond site is the expected mode of failure. In general the closer the recess approximates to the shape of the deposit, the more likely is shear failure at the interface between the deposit and the substrate. However if shear failure at the bond interface can be achieved using a tool of simple form, a more complex form may not be necessary. What is required will depend on the type of material to be tested and the nature of the bond at the inter metallic interface; this can be determined empirically using techniques to be described later in the specification.

In a preferred embodiment the recess is a part-cylindrical, preferably semi-cylindrical cavity having a diameter within which will closely fit at least 75% and most preferably 95% of all deposits to be tested. Such cavity ensures that reshaping of oversize or undersize deposits is minimised. However gold and solder are relatively soft materials, and a small amount of reshaping can be accommodated without significant alteration of the bond interface. Preferably reshaping of the deposit occurs over 30% or less of the circumference of the deposit. In the case of very precisely formed deposits, the recess can closely approach the ideal diameter for a line contact or a narrow band contact with minimal reshaping.

A small amount of reshaping may be beneficial in that the deposit can more closely conform to the shape of the recess. Such reshaping is preferably limited to a depth of less than 10% of the diameter of the deposits, and most preferably less than 5%.

Other features of the invention will be apparent from the following description of a preferred embodiment shown by way of example only in the accompanying drawings, in which:

FIG. 6 illustrates in elevation a section through a test head according to the invention;

FIG. 7 illustrates the test head of FIG. 6 in transverse section;

FIG. 8 illustrates deformation of a gold deposit due to the test head of FIG. 6 in elevation;

FIG. 9 illustrates deformation of a gold deposit due to the test head of FIG. 6 in plan.

FIGS. 10 and 11 correspond to FIG. 8 and 9 but show a solder deposit.

In the accompanying drawings, some clearances are somewhat exaggerated for reasons of clarity.

Figure 1:
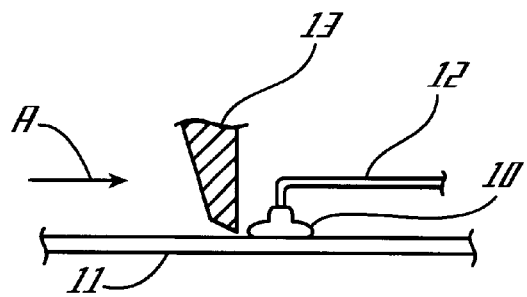
FIG. 1 illustrates in elevation, a section through a prior art chisel test head.
Figure 2:
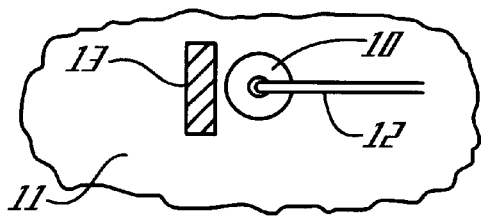
FIG. 2 illustrates a transverse section through the prior art chisel test head.

With reference to FIG. 1 and 2, a gold wire 12 having a balled end is connected to a substrate 11. An inter metallic bond forms between the deposit 10 and the substrate, and provides both a mechanical and electrical connection.

Figure 5:
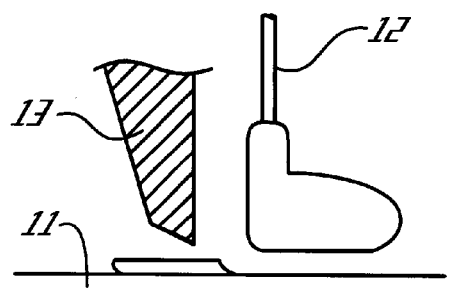
FIG. 5 illustrates the deposit of FIG. 4 after breakage.

Single point contact causes a high initial load which in practice causes the shear tool to cut into the relatively soft material of the deposit. This results in a straight line indentation which promotes breakage (as illustrated in FIG. 5).

In order to test the mechanical strength of the bond between the deposit and substrate, a flat shear tool 13 is moved in the direction of arrow A and applied to the side of the deposit 10. Eventually either the deposit or the bond will break, but because the tool 13 contacts the deposit 10 initially at a single point, the former is more likely. If the deposit breaks above the inter metallic bond, the force necessary to shear the deposit from the substrate cannot be determined. The force required to break the bond or break the deposit can be determined by for example conventional strain gauge techniques.

In the drawings, the distance of the shear tool 13 above the substrate 11 is exaggerated, but nevertheless the application of the flat tool to the curved surface of the deposit makes breaking of the deposit more likely, not least because the tool may cut into or otherwise distort the deposit.

Figure 3:
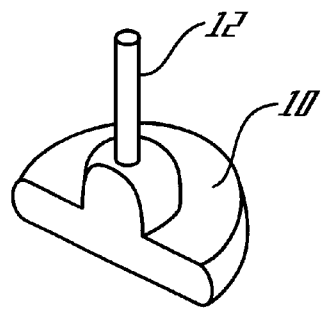
FIG. 3 illustrates a prior art deposit after testing.
Figure 4:
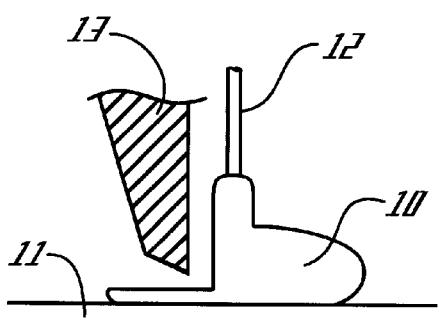
FIG. 4 illustrates in section a prior art deposit during testing.

FIG. 3 illustrates the typical deformation experienced by a gold deposit when contacted by a flat shear tool 13. Typically up to one third of the diameter of the deposit will be flattened by the face of the tool. As illustrated in FIG. 4, because of the necessary clearance between the tool and the substrate, the tool may in fact chisel the deposit above the inter metallic bond, thus resulting in breakage partially above the plane of the bond itself. (FIG. 5).

This deformation is undesirable, but since flat shear tools are relatively easy to make, they are used for shear testing, notwithstanding the disadvantages thereof.

In the case of solder deposits, the solder adopts a generally hemispherical shape compared with the squashed ball appearance of a gold bond. The effects of a shear tool are however rather similar. Some solder deposits are approximately an order of magnitude larger than a gold deposit, and other methods of the testing are thus practicable. For example a solder deposit of typically 750 $\mu$m in diameter may be gripped by tweezers for a tensile test of the bond strength. However, a gold deposit or a small solder deposit, typically 75 $\mu$m in diameter, is too small to be gripped in this way, and a shear test is at present the only practical test.

The invention illustrated in FIGS. 6 and 7. In this case the shear tool 14 is provided with a cylinder recess 15 at the base thereof, the diameter of the recess 15 being appromaximately the same as the diameter of the deposit 10.

The cylinder cavity tool 14 provides at least a line contact on the deposit and accordingly the high initial point load of the flat tool 13 is avoided, along with the subsequently major deformation of the deposit. In practice the cavity tool 14 may cause a slight flattening of the edge of the deposit, to give the appearance illustrated in FIG. 8 and 9 for a gold deposit. A relatively narrow band 16 is formed around part of the circumference by deformation.

In the case of a solder deposit, the deformation may have the typical appearance illustrated in FIGS. 10 and 11. The band 17 in this case is in the form of a slight indentation, due to the dome-like form of the solder deposit. Solder deposits can also be substantially more sphere like, and in that case a flat band similar to FIG. 8 may be expected at the contact area

EXAMPLE ONE

In one comparative test, deposits of gold in the diameter range 70–90 $\mu$m were tested with a tool having a cylindrical cavity. The height of tool above the substrate was varied. The maximum applied load using the cylindrical cavity tool was typically 9% greater than for a conventional flat tool. This increased load resulted in a reduced proportion of deposit breakage, and is illustrated in the following table which shows the percentage of tests in which all deposit was removed (thus indicating pure shear at the intermetallic bond).

| | Percentage with no deposit remaining | |
|---|---|---|
| Height above substrate ($\mu$m) | Flat Tool | Cavity Tool |
| 1 | 15 | 75 |
| 2 | 0 | 80 |
| 3 | 40 | 75 |
| 4 | 10 | 90 |
| 5 | 5 | 55 |

Examination of the deposits after testing typically showed a significant flat face caused by deformation due to the flat tool (FIGS. 3 and 4), whereas the cavity tool left the deposit much less deformed. (FIG. 8 & 9). Deformation due to the flat tool plainly causes the internal structure of the deposit to be affected, not least by causing the deposit to break at a lower force than is required to test the strength of the intermetallic bond. It must be emphasised that the drawings are representative, due to the very small size (c. 75 $\mu$m) of the deposits tested.

EXAMPLE 2

A second representative test was carried out using solder deposits of 730 $\mu$m and 750 $\mu$m diameter, and a tool having a cylindrical cavity.

| | Mean test force to breakage (grams) | | | |
|---|---|---|---|---|
| Height above | 730 $\mu$m diameter | | 750 $\mu$m diameter | |
| substrate ($\mu$m) | Flat Tool | Cavity Tool | Flat Tool | Cavity Tool |
| 20 | 1191 | 1248 | 1490 | 1574 |
| 130 | 1158 | 1224 | 1452 | 1568 |

Applied loads for cavity shear tools were again higher, 4.8% and 8% respectively.

In all cases the deposits sheared through the solder above the substrate close to but not at the intermetallic bond. The load sustainable by the solder deposit is thus insufficient to ensure breakage at intermetallic bond, but it is a significant improvement over prior test methods. Considerable deformation occurred for the flat tool, typically a flat face approximately at an indentation of about 35% of the diameter of the deposit. The cavity tool caused little deformation, as illustrated in FIGS. 10 and 11. The applied load was not sufficient to shear the solder at the intermetallic interface, but nevertheless indicates that the bond has a higher strength than can be tested by a conventional flat tool.

What is claimed is:

1. A test for shear testing of electrical conduction deposits of semiconductor devices, said deposits having substantially the shape of a dome and having a diameter in the range of 50–1000 $\mu$m, said test device comprising a test head having a recess preformed to closely engage said deposit over part of the circumference thereof for the application of a shear force.

2. A test device according to claim 1 wherein said recess closely engages the deposit over part of the surface thereof.

3. A test device according to claim 2 wherein said recess is semicircular.

4. A test device according to claim 3 wherein said recess is a semi-cylindrical cavity having a diameter adapted to closely fit at least 75% of a range of deposits to be tested.

5. A test device according to claim 4 wherein said recess is adapted to closely fit at least 95% of a range of deposits to be tested.

6. A test device according to claim 1 wherein said recess is adapted to closely engage the deposit over 30% or more of the circumference thereof.

7. A method of shear testing a plurality of part-spherical deposits on a substrate, the deposits being of gold or solder and for bonding of electrical conductors thereto, the method comprising the steps of:

determining the mean radius of said deposits;

selecting a shear test tool having a preformed semi-cylindrical cavity approximately equal to said mean radius;

applying said test tool to each deposit in turn to shear said deposits from said substrate; and measuring the shear force to shear said deposits from said substrate.

8. A method according to claim 7 and further including the intermediate step of causing the test tool to partly reshape deposits which are not of the mean radius prior to shearing said deposits, the reshaped deposits conforming closely to the cavity of said test tool.

9. A method according to claim 8 wherein said re-shaping occurs over 30% or less of the circumference of a respective deposit.

10. A method according to claim 9 wherein said reshaping is limited to a depth of 10% of the diameter of a respective deposit.

* * * * *